United States Patent [19]

Dybas et al.

[11] 4,402,959
[45] Sep. 6, 1983

[54] ANTIMICROBIAL COMPOSITIONS

[75] Inventors: Richard A. Dybas, Piscataway; Bruce E. Witzel, Rahway, both of N.J.

[73] Assignee: Merck & Co., Inc., Rahway, N.J.

[21] Appl. No.: 325,090

[22] Filed: Nov. 25, 1981

Related U.S. Application Data

[63] Continuation-in-part of Ser. No. 155,331, Jun. 2, 1980, abandoned.

[51] Int. Cl.$^3$ .............................................. A01N 43/48
[52] U.S. Cl. ...................................................... 424/250
[58] Field of Search ......................................... 424/250

[56] References Cited

U.S. PATENT DOCUMENTS

| 3,274,192 | 9/1966 | Cragoe, Jr. et al. | 260/250 |
|---|---|---|---|
| 3,299,063 | 1/1967 | Cragoe, Jr. et al. | 260/250 |
| 3,341,540 | 8/1967 | Cragoe, Jr. et al. | 260/250 |
| 3,487,082 | 10/1967 | Cragoe, Jr. et al. | 260/251.5 |
| 3,626,060 | 12/1971 | Grier | 424/232 |
| 3,763,176 | 10/1973 | Kohn et al. | 260/382 D |
| 3,854,000 | 12/1974 | Kohn et al. | 424/220 |
| 4,054,655 | 10/1977 | Donald | 424/250 |
| 4,119,779 | 10/1978 | Grier et al. | 544/215 |
| 4,145,426 | 3/1979 | Grier et al. | 424/267 |

OTHER PUBLICATIONS

J. Perchais, et al., Tetrahedron Letter 30, 999–1009 (1974).

Primary Examiner—Allen J. Robinson
Attorney, Agent, or Firm—Alice O. Robertson; Raymond M. Speer

[57] ABSTRACT

Antimicrobial compositions for use in agriculture and methods of treatment are disclosed. The compounds are 3-amino-5,6-dihalopyrazine-2-carbonitrile.

3 Claims, No Drawings

ANTIMICROBIAL COMPOSITIONS

REFERENCE TO RELATED APPLICATIONS

This is a continuation-in-part of application Ser. No. 155,331, filed June 2, 1980 and now abandoned.

The present invention relates to improved antimicrobial compositions for use in agriculture, as for the treatment of plants and foliage and also of soil and of seeds, including the crop at any stage of its growth.

It is the general object of the invention to provide antimicrobial compositions characterized by a high degree of effectiveness in relatively low concentrations, against various fungi and bacteria encountered in agriculture, this high activity being coupled with substantial absence of phytotoxicity within the effective range of antimicrobial activity.

The present invention is of particular utility in the treatment of plants and soils infected or subject to injection by various destructive fungi, while at the same time there is obtained by its use a pronounced growth-stimulating action producing not only an abundant root system but also a luxuriant growth above ground, this being accompanied by a substantial increase in the yield of the crop per acre as compared not only with untreated plants and soils, but also with other, widely used foliar and soil fungicides.

It is accordingly a further object of the invention to provide foliar and soil fungicides which are characterized by a high degree of effectiveness, so that comparatively small amounts thereof need be applied per acre, while at the same time no damage to the foliage, seeds, or root systems in plants of various kinds is promoted and likewise a heavy and high crop-yielding growth both below and above ground.

It is also an object of the invention to provide a foliar and soil fungicide which can be marketed in a highly concentrated form and is adapted for easy dilution with large quantities of water in which it is quite homogenously distributed for uniform application to large areas by spraying, or otherwise.

It is a still further object of the invention to provide fungicidal (and fungistatic), and bactericidal (and bacteristatic) preparations which can be used both for soil sterilization and for protection of seeds upon planting as well as in storage, and also on the foliage and fruit or vegetable crops themselves, for promoting a high percentage of germination and a healthy and abundant, growth.

Other objects and advantages of the invention will appear from the following more detailed description thereof.

In accordance with the present invention there are employed as soil, seed and plant (including crop) fungicides and bactericides (by which terms are understood also fungistats and bacteriastats) having as their active entity a compound of the formula:

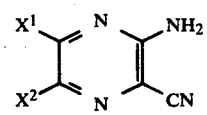

where $X^1$ and $X^2$ are halo, especially chlorine or bromo.

The compounds employed in the compositions of the present invention are useful in the destruction and inhibition of fungi and bacteria while being at the same time substantially nonphytotoxic within their active concentrations and are indicated for the protection of soil, seeds, roots, and foliage of plants and their crops against fungal and bacterial infestation and attack.

A further advantage which distinguishes the preparations of the present invention from many known and commercially employed fungicides is that, the compounds of the present invention are easy to handle, have no odor, have no lachramatory effect, and do not have a high vapor pressure.

A still further advantage of the compounds employed in the present invention arises from the fact that they are free of toxic metals, like mercury and copper, so that such metals do not accumulate in the soil with repeated use.

Among the compounds within the scope of the invention which have been found to be active against various destructive fungi and bacteria are the following:
3-amino-5,6-dichloropyrazine-2-carbonitrile;
3-amino-5,6-dibromopyrazine-2-carbonitrile;
3-amino-5-bromo-6-chloropyrazine-2-carbonitrile; and
3-amino-5-chloro-6-bromopyrazine-2-carbonitrile.

Antimicrobial compositions suitable for application to inantimate surfaces of growing plants, or crops which contain the fungicidal compounds of this invention may be compounded in a variety of conventional formulations. However, such formulations must take account of the solubility characteristics of the 3-amino-5,6-dihalopyrazine-2-carbonitrile antimicrobial compounds utilized in the present invention. For example, the dihalopyrazines are soluble in paraffinic oils such as xylene to an extent of less than 2%, whereas solubility of the order of 20 to 40% would be required to employ such oils as formulation media. On the other hand, such oils as do provide the required solubility for the dihalopyrazines are not useful in preparing agricultural formulations because of cost, toxicity, etc.

The dihalopyrazine antimicrobial compounds utilized in the present invention can be formulated as suspension concentrates or "flowable" formulations in either an oil or water base. Such formulations must include the proper amounts and types of suspending agents or emulsifiers, and preferably also stabilizers, spreading agents, and sticking agents. Well-known techniques and materials are employed in preparing these formulations. Suitable emulsifiers or suspending agents include both cationic and nonionic compounds such as sodium alkyl sufates ("Dreft"), alkyl and alkyl-aryl sulfonates ("Nacconal N.M." and Dupont "MP-189"), alkyl-aryl polyester alcohols ("Spans"), and ethylene oxide addition products ("Tweens"). The nonionics are the preferred surfactants and include alkylphenol-ethylene-oxide condensation products such as isooctylphenol-polyethylene oxide condensates ("Triton X-100"), the various "spans" (sorbitan monopalmitate, stearate or oleate) and "Tweens" (e.g., sorbitan monolaurate-"Tween 20"). These materials can constitute from 0.05 to 10 percent of the active agents.

It is desirable to include a sticking agent or adhesive in the composition in the range of about ½ to 5 percent of the active material. These adhesives can be in the form of resins which are soluble or dispersible in water, and include cellulose ethers, waxes, polyvinyl pyrrolidine, and powdered polyethylene. Sticking agents may also be included in small proportion (about ½ to 5 percent of the active substance), these including glycerin and nonvolatile polyethylene glycols.

For agricultural use these formulations may be diluted with water and applied to the foliage or soil. Adjuvants can be mixed with the active material before use or they may be sold as such in the dry condition admixed with the active material. The mixture then may be added to water just prior to use.

The emulsifying or suspending agents all, both singly and in admixture, serve the function of uniformly distributing the active ingredient in the aqueous or organic emulsions or suspensions, marketed as concentrates so that on mixing with water by the user there is produced a uniform mixture for application to the soil, seeds or plants.

The dihalopyrazines utilized in the present invention may also be formulated as wettable powders.

For formulating wettable powders, various adjuvants and suspending agents can be employed such as are listed in Soap and Chemical Specialties, Volume 31, Number 7, p. 61 Ed. Seq.; No. 8 pp. 48–61; No. 9, pp. 52–57 and No. 10 pp. 38–67 (1955) and in Bulletin No. 607 of the Bureau of Entomology and Plant Quarantine, Department of Agriculture Washington, D.C. The suspending agents include detergents of various kinds.

In the form of liquid concentrates or wettable powders as described above, the active component can comprise from 5 to 90 percent by weight of the composition, the remainder being the liquid carrier which can include any of the agents discussed above.

The dihalopyrazines may also be formulated as dusts or granular formulations.

For use in the form of a dust or granular formulation the dihalopyrazines may be blended with any suitable proportion of a variety or excipients including diluents, suspending and spreading agents and other adjuvants in pulverulent form (preferably below 50 micron particle size). Usually, the inert carrier will range in percentage composition from about 1 to 80 percent of the total composition and will include about one to five parts of a dispersing agent for 100 parts of active compound.

Suitable diluents include natural clays such as china clays, talc, bentonite, attapulgites and other similar inert material, and also pyrophyllites, diatomaceous earth, fuller's earth, chalk, rock phosphates, and also chemically modified minerals such as acid-washed bentonite, precipitated calcium phosphate and carbonate, colloidal silica, mica, pumice, vermiculite, wood flour, and grain flours. There can also be employed inert metal oxide and hydroxides such as titanium dioxide, aluminum oxide, and bauxite. Diluents such as clays, talc, bentonite and other mineral powders may be oil treated to increase their adhesivity; the oil being either a mineral hydrocarbon oil or a vegetable oil or an animal fatty oil.

The dihalopyrazines utilized in the present invention may also be formulated as solutions in gammabutyrolactone or N-methylpyrrolidinone. These solutions may be used as such or may additionally include additives of the types described in detail above. These solutions may also serve as the basis for other types of formulations as described in detail above.

The compositions can include various insecticides which are nonreactive with the fungicide.

Typical formulations are presented below, but it is to be understood that they are given by way of illustration only and not as indicating the scope of the invention.

EXAMPLE A

| Wettable Powder | Parts by Weight |
| --- | --- |
| Finely particled clay | 48 |
| Alkyphenoxypolyethoxyethanol (wetting agent) | 2 |
| 3-amino-5,6-dichloropyrazine-2-carbonitrile | 50 |

Five to 10 lbs. of the above mixture are stirred into 30 to 90 gallons of water per acre and sprayed onto foliage.

EXAMPLE B

| Emulsifiable Liquid | Parts by Weight |
| --- | --- |
| Dipropyleneglycolmonomethyl ether | 50 |
| Anhydrous xylene | 40 |
| Alkylphenoxypolyethoxyethanol | 5 |
| 3-amino-5,6-dichloropyrazine-2-carbonitrile | 5 |

Fifty to 100 lbs. of the liquid preparation are emulsified with 30 to 60 gallons of water per acre for spraying on foliage.

EXAMPLE C

Concentrated pastes may be prepared by mixing finely powdered 3-amino-5,6-dichloropyrazine-2-carbonitrile with methylcellulose and small amounts of sodium ligninsulfonate. The resulting powder blend is then stirred with sufficient water to give pastes of desired viscosity.

|  | Parts |
| --- | --- |
| 3-amino-5,6-dichloropyrazine-2-carbonitrile | 95 |
| Methylcellulose | 2 |
| Sodium Ligninsulfonate | 3 |

The paste, which is prepared by simply mixing the powder with cold water, can then be used to make dispersions in water by simple dilution. The resultant suspensions can then be used as agricultural sprays.

Generally, it is best to apply the composition to the top of the ground and then turn the soil over. Thus, 60 gallons of water can contain 5 pounds of the active substance to be applied per acre, this yielding 5 p.p.m. when the soil is turned over to a depth of 3 inches. (At a 3 inch depth, 1 pound of antibacterial substance per acre is equivalent approximately to 1 p.p.m.) In case of cotton, for which the soil need be turned over for only a 2" depth, a correspondingly smaller amount of the active compound need be used. On the other hand, when the soil is plowed or turned over to a depth of 6", as for potatoes, a correspondingly larger amount is used.

As above indicated, the active material can be applied either in the form of a slurry or suspension or as a dust.

As disclosed above, the compounds of the invention are not phytotoxic in the effective ranges in which they are to be used. The concentrations at which damages to seeds or plants occur is so much higher than the effective ranges that the danger is practically nonexistent in view of the large spread between the effective and phytotoxic concentrations.

Both in the powdered and in the liquid forms, the compositions of this invention can be used as seed dressing to destroy seed-borne fungus spores and bacteria, both to increase the percentage germination and to protect the young plants and roots systems. Further, young plant roots can be dipped in such compositions to protect them against fungal attack.

The compositions of the present invention can be used with advantage in sterilizing the soil on which are grown various vegetables, fruits and other agricultural products, such as beans, soy beans, sugar beets, carrots, cucumbers cabbage, corn, peanuts, tomatoies, cotton, alfalfa, oats and clover, among others, and can also be applied to seeds and plants to protect them against destructive micro-organisms.

The compositions according to the present invention possess not only antifungal but also antibacterial activity.

The new compositions are effective also against the various fungi that infest fruit trees. Thus apple trees can be sprayed, before fruit set, with an aqueous suspension, prepared by mixing, say, 100 gallons of water with an amount of the commercially prepared composition containing the active compound embraced in this specification such that 5 to 20 p.p.m. are contained in the spray suspension. In this way there can be controlled, for example, the apple scab fungus *Venturia inaequalis*. Other fruit trees like peach and cherry, can be treated in similar fashion.

What is claimed is:

1. A method for protecting soil, seeds, plants and crops against destructive fungi and bacteria which comprises applying there an antifungal and antibacterial quantity of a composition comprising an agricultural carrier and 5 to 95 percent of a bactericidally and fungicidally effective compound of the formula:

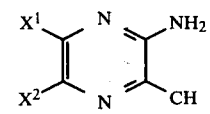

where $X^1$ and $X^2$ are halo.

2. A method according to claim 1 wherein $X^1$ and $X^2$ are chloro.

3. A method according to claim 1 wherein $X^1$ and $X^2$ are bromo.

* * * * *